United States Patent [19]

Singer

[11] Patent Number: 4,479,492
[45] Date of Patent: Oct. 30, 1984

[54] BILATERAL SPLIT SURGICAL DRAPE

[75] Inventor: Wayne J. Singer, Outagamie County, Wis.

[73] Assignee: Kimberly-Clark Corporation, Neenah, Wis.

[21] Appl. No.: 449,286

[22] Filed: Dec. 13, 1982

Related U.S. Application Data

[63] Continuation of Ser. No. 200,324, Oct. 24, 1980, abandoned.

[51] Int. Cl.³ .............................................. A61F 13/00
[52] U.S. Cl. ................................................. 128/132 D
[58] Field of Search ........................ 128/132 D, 132 R

[56] References Cited

U.S. PATENT DOCUMENTS

| | | | |
|---|---|---|---|
| D. 256,161 | 7/1980 | Oliver | D24/4 |
| 3,072,511 | 1/1963 | Harwood | 154/46 |
| 3,343,534 | 9/1967 | Keoughan et al. | 128/132 D |
| 3,484,330 | 12/1969 | Sokolowski et al. | 161/59 |
| 3,503,391 | 3/1970 | Melges | 128/132 |
| 3,668,050 | 6/1972 | Donnelly | 161/39 |
| 3,669,106 | 6/1972 | Schrading et al. | 128/132 |
| 3,797,484 | 3/1974 | Ericson | 128/132 D |
| 3,799,161 | 3/1974 | Collins | 128/132 |
| 3,910,268 | 10/1975 | Miller | 128/132 |
| 3,926,185 | 12/1975 | Krzewinski | 128/132 D |
| 3,930,497 | 1/1976 | Krebs et al. | 128/132 |
| 3,942,523 | 3/1976 | Rudtke | 128/132 |
| 4,027,665 | 6/1977 | Scrivens | 128/132 |
| 4,041,203 | 8/1977 | Brock et al. | 428/157 |
| 4,041,942 | 8/1977 | Dougan et al. | 128/132 D |
| 4,196,723 | 4/1980 | Moose, Jr. | 128/132 |

Primary Examiner—C. Fred Rosenbaum
Assistant Examiner—C. W. Shedd
Attorney, Agent, or Firm—William D. Herrick; R. Jonathan Peters; Howard Olevsky

[57] ABSTRACT

A surgical drape for use in procedures requiring exposure of both legs and containment of the perineum comprised of a flexible draping material, a second smaller sheet of foam/film laminate bonded to the first sheet with two elongated fenestrations formed through both layers of sheets. The elongated fenestrations open onto one end of the drape and extend toward the middle of the drape in alignment with the sides and with each other and spaced apart to receive the legs of a patient. The drape is folded to form a compact unit for storage and sterilization and in a manner that unfolding and application of the drape to the patient can be accomplished with a minimum chance of contamination.

2 Claims, 15 Drawing Figures

BILATERAL SPLIT SURGICAL DRAPE

This is a continuation of application Ser. No. 200,324 filed Oct. 24, 1980 now abandoned.

BACKGROUND OF THE INVENTION

1. Field of the Invention

This invention relates broadly to surgical cover means and particularly to a new and improved surgical drape for operations requiring exposure of both legs of a patient while covering other parts of the patient and the operating table.

2. Description of the Prior Art

One drape that has been used for many types of surgery including operations on limbs comprises a sheet having one elongated fenestration opening onto one end of the sheet extending inwardly toward the middle of the sheet. Such drapes are frequently referred to as "split sheet" drapes. Examples of such single fenestration drapes are taught in U.S. Pat. Nos. 3,930,497 to Krebs and Arps issued Jan. 6, 1976; U.S. Pat. Nos. 3,910,268 to Miller issued Oct. 7, 1975; and 3,669,106 to Schrading and Winters issued June 13, 1972.

The normal procedure used to expose a limb for surgery using a split sheet drape is to raise the limb and place the split sheet under and around the limb so that it is received by the fenestration and rests on the solid portion of the drape and the end flaps formed around the fenestration are overlapped and secured to the body and each other by adhesive, suture or clips.

When exposure of both legs is required, two split sheets must be separately applied to each leg of the patient. This requires added time in the draping procedure and further delays the operation. There is also excess bulk and waste of draping material, many areas of the patient's body being covered by more layers of material than necessary. The excess weight and bulk of the draping material may also cause excessive heat build-up and discomfort to the patient.

In addition to the normal possibility of contamination in a draping procedure, there is the added danger of contact with the highly contaminated perineal area since placement of the split sheet drapes necessitates manipulation by operating room personnel of both sheets in that area. If contamination does occur during draping or is suspected to have occurred, all new drapes must be applied causing an additional waste of time and material. Contamination by the perineal area is in fact so feared with this procedure that it is common practice for operating room personnel to "double glove". They wear two pairs of gloves during application of the drapes and remove one pair after draping.

Prior art workers have developed various surgical drapes and sheets with two or more fenestrations for use in various types of surgical procedures, as in U.S. Pat. No. D. 256,161 to Oliver issued July 29,1980; U.S. Pat. No. 4,196,723 to Moose issued Apr. 8, 1980; U.S. Pat. No. 4,027,665 to Scrivens issued June 7, 1977; U.S. Pat. No. 3,942,523 to Rudtke issued Mar. 9, 1976; U.S. Pat. No. 3,799,161 to Collins issued Mar. 26, 1974; and U.S. Pat. No. 3,503,391 to Melges issued Mar. 31, 1970. However, none of these drapes is taught as specifically adapted for use in bilateral leg surgery as is the present dual fenestration split drape claimed herein.

SUMMARY

This invention provides an improved surgical drape having two elongated fenestrations for receiving and exposing both of a patient's legs during bilateral leg surgery. This eliminates the need for applying two split sheets thus saving time and money. The folding of the drape and its configuration also facilitate an easy and fast method of application such that sterile surfaces and operating room personnel avoid contact with non-sterile surfaces, especially the perineal area.

DESCRIPTION OF THE PREFERRED EMBODIMENTS

While the invention will be described in connection with preferred embodiments, it will be understood that it is not intended to limit the invention to those embodiments. On the contrary, it is intended to cover all alternatives, modifications, and equivalents as may be included within the spirit and scope of the invention as defined by the appended claims.

Figure 1:
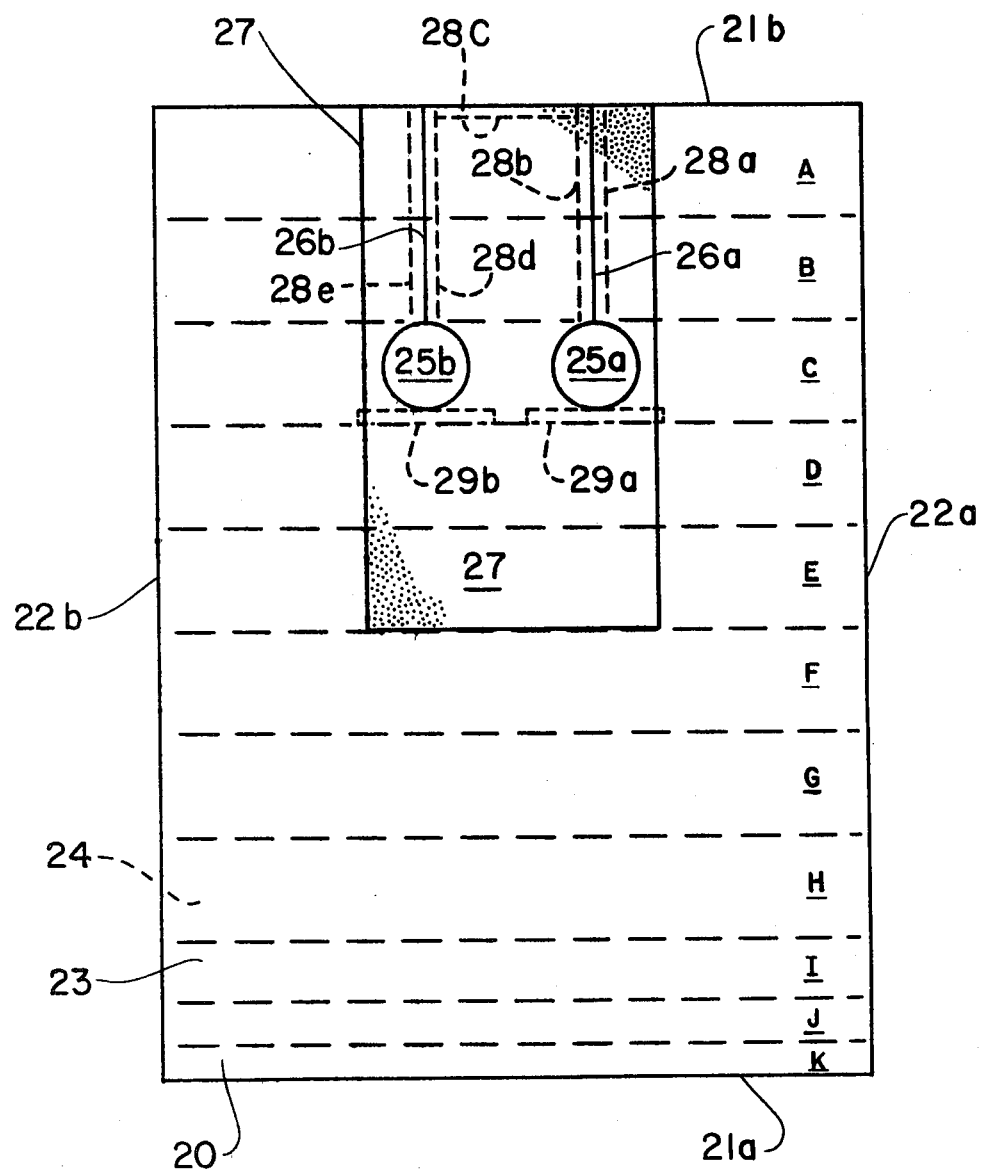
FIG. 1 is a top plan view of the drape of the present invention showing the position of the adhesive strips, fenestrations, foam/film laminate and lateral fold lines.

Referring now to FIG. 1, which shows one embodiment of the surgical drape, the invention includes a base sheet 20 which is formed from liquid repellent drapable material, preferably a disposable nonwoven fabric. Examples of suitable fabric include scrim reinforced tissue products under the trademark KAYCEL® from Kimberly-Clark Corporation described for example, in U.S. Pat. No. 3,072,511 to Harwood issued Jan. 8, 1963, assigned to the assignee of the present invention. Also the nonwoven fabic described in U.S. Pat. No. 4,041,203 to Brock and Meitner issued Aug. 9, 1977; and U.S. Pat. No. 3,484,330 to Sokolowski, Lewis, and Hrubecky issued Dec. 16, 1969, both patents assigned to the assignee of the present invention, may be used.

As illustrated in FIG. 1, the base sheet 20 has a pair of side edges, 22a and 22b; a pair of end edges, 21a and 21b; a top surface 23 which faces away from the operating table after application of the drape to the patient; and a bottom surface 24 which faces toward the operating table after application of the drape to the patient.

Between the side edges, 22a and 22b, and opening onto end edge 21b are two longitudinal fenestrations. In its preferred form to better accomodate the legs, the fenestrations of the drape are composed of a circular part; 25a and 25b in the central area of the drape, and a slit, 26a and 26b joining the circular part of the fenestrations to the end edge 21b. The fenestrations, however, may be in the configuration of a U-shape gap with a slightly poorer fit around the legs after application of the drape.

In a particularly preferred embodiment, bonded to the top surface 23 of the base sheet is a smaller sheet of foam/film laminate 27 approximately the same shape as the base sheet with two longitudinal fenestrations which conform to and align with the two fenestrations of the base sheet. The foam/film laminate is desirably of the type described in U.S. Pat. No. 3,699,106 to Schrading and Winters issued June 13, 1972, and U.S. Pat. No. 3,668,050 to Donnelly issued June 6, 1972, both patents assigned to the assignee of the present invention. It may include a film such as anti-static polyethylene, polypropylene, polyethylene methylacrylate copolymer, and vinyl chloride films bonded to the base sheet 20 by any suitable means such as adhesive or by extruding the film directly on the base sheet. The film provides a fluid impervious barrier on the top of the operative area of the base sheet so that any liquid which contacts the sheet will not strike through. It also prevents the transfer of bacteria through the base sheet.

Bonded to the film of the foam/film laminate is a fluid absorbent flexible plastic foam material. The foam may be bonded to the film by any suitable means such as adhesive, fusing or by extruding the film directly on the foam. Examples of suitable foams are polyester polyurethane foams and polyether polyurethane foams. The foam thickness should be generally in the range of from 25 mils to about 100 mils. The absorbent foam prevents excess fluid runoff, while the film keeps the absorbed fluid from striking through the base sheet.

Attached to the bottom side 24 of the drape are several tacky, pressure sensitive adhesive strips which will face and contact the patient's body after application to hold the drape in place during the operation. Release strips cover the adhesive strips to prevent adhesion during packaging and application until removed at the appropriate time in the draping procedure.

The adhesive strips are bonded to the base sheet 20 and are desirably of the type described in U.S. Pat. No. 3,669,106 to Schrading and Winters issued June 13, 1972 and assigned to the assignee of the present invention. The tacky and pressure sensitive adhesives used may be of any biologically acceptable adhesives available. These adhesives are generally made of a film-foam elastomer and some type of resin or other material to impart the desired adhesion properties.

The release strips covering the adhesive layer of the bonded adhesive strips are a plastic, heavy paper or nonwoven fabric having a release coating to which the adhesive only slightly adheres. Suitable coatings include natural or synthetic waxes, metal salts or fatty acids, polymeric materials such as polyethylene or silicone polymers.

In FIG. 1 the adhesive and release strips are designated 28a, 28b, 28c, 28d, 28e, 29a and 29b. In the preferred embodiment tapes 28a and 28b surround and are substantially co-extensive with slit 26a and tapes 28d and 28e surround and are substantially co-extensive with slit 26b. These tapes are used to adhere to the patient and to overlap closing the slits. Tape 28c faces onto and is substantially coextensive with end edge 21b between slits 26a and 26b and will adhere to the patient. Tapes 29a and 29b are placed opposite the slits near the edge of the circular element 25a and 25b respectively. These tapes are used to adhere the fenestration to the underside of the patient's legs. Tape may alternatively be placed around and substantially co-extensive with the edges of the circular elements to adhere around the entire circumference of each leg. In other embodiments of the drape in which the fenestrations are differently shaped, adhesive tape is applied around the fenestration edges.

The drape will normally be rectangular as shown with dimensions sufficient to cover the patient's body. Sides 22a and 22b are longer than ends 21a and 21b.

Folding of the Drape

Drapes of the present invention may be folded to form a compact unit for storage and sterilization and in a pattern to facilitate application to the patient.

For convenience, panels and folds in parallel alignment with side edges will be designated as longitudinal and those parallel to end edges will be designated as lateral. The drape will first be folded along the lateral folds to facilitate application and reduce size and then along the longitudinal folds to reduce the size.

As shown in FIG. 1 panels A, B, C, D, E, F, G, and H are of the same dimensions. Panel I is approximately ½ the width of H, panel J is approximately ½ the width of I, and panel K is approximately ½ the width of J. However, this pyramiding of widths in the last lateral panels of the drape is only to compensate for extra length in the drape due to variances in production runs. For example, if the drape is shorter there may only be panels A through I. It is only necessary that the last panel on end edge 21a be of such a width that the panel when folded forms a flap in approximately the middle of panel H so that when the end edge is grasped to unfold the drape contact is only made with a sterile surface of the drape.

Figure 2:
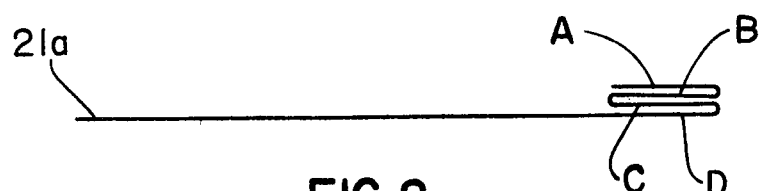
FIG. 2 is a cross sectional view and FIG. 3 a perspective view of the first lateral folding step.
Figure 3:
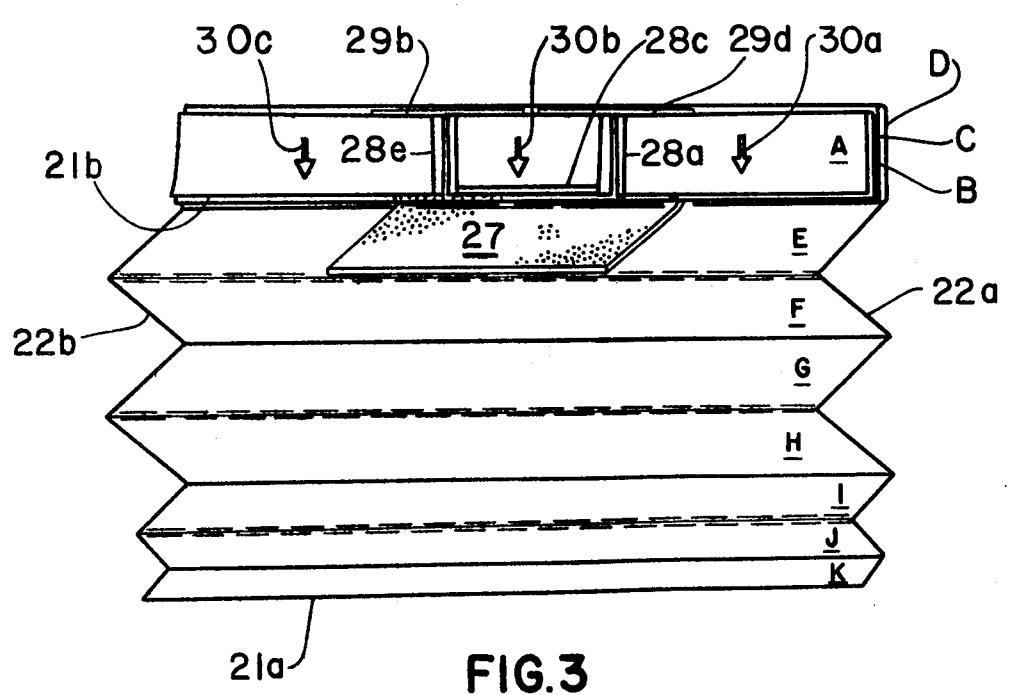

The first step in lateral folding is to enclose the fenestration area of the drape so that when the drape is applied it will be the last area unfolded. This will be accomplished by making folds between panels A, B, C, and D so that the top surface of panel A rests on the top surface of panel B; the bottom surface of panel B rests on the bottom surface of panel C; and the top surface of panel C rests on the top surface of panel D as shown in side view in FIG. 2 and top view in FIG. 3. As shown in FIG. 3, arrows 30a, 30b and 30c are printed on the bottom surface of panel A pointing toward the end edge 21b to indicate direction to unfold for application.

Figure 4:
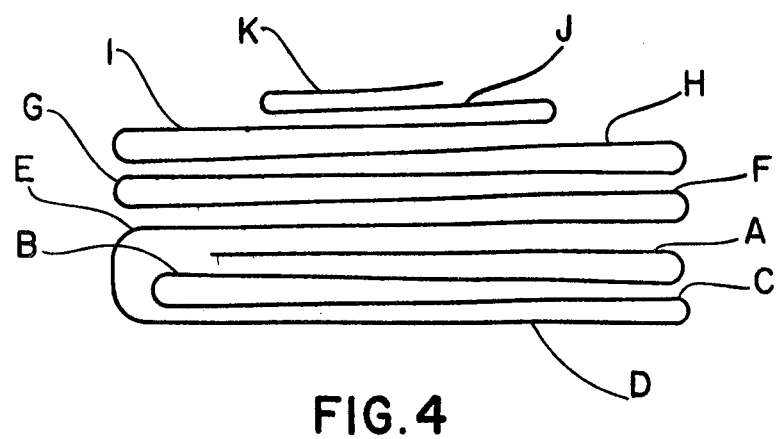
FIG. 4 is a cross sectional view and FIG. 5 a top plan view of the surgical drape after lateral folding is completed.
Figure 5:
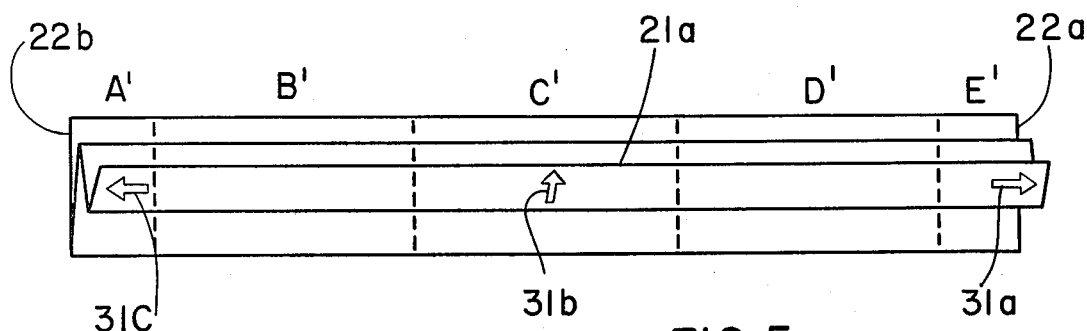
FIG. 5 also indicates the position of longitudinal foldlines and printed arrows to indicate direction of unfolding.

The second step in lateral folding will further enclose the fenestration area and reduce the size of the drape. The drape is folded between panels D, E, F, G, H, I, J, and K so that the top surface of panel E rests on the bottom surface of panel A; the bottom surface of panel F rests on the bottom surface of panel E; the top surface of panel G rests on the top surface of panel F, the bottom surface of panel H rests on the bottom surface of panel G, the top surface of panel I rests on ½ of the top surface of panel H; the bottom surface of panel J rests on ½ of the bottom surface of panel I, and the top surface of panel K rests on ½ of the top surface of panel J. When completed the drape will appear as side view in FIG. 4 and as top view in FIG. 5. Arrows 31a, 31b, and 31c shown in FIG. 5 are printed on the bottom surface of panel K with 31a and 31c pointing out to sides 22a and 22b respectively and 31b pointing to end edge 21a to indicate directions in unfolding.

The drape is now folded longitudinally to reduce the bulk of the drape for packaging. FIG. 5 shows five longitudinal panels A', B', C', D', and E', defined by longitudinal fold lines. Panels B', C', and D' are of equal dimensions and panels A' and E' are of equal dimensions with panels A' and E' having shorter lateral sides than B', C', and D'. It is necessary that the lateral dimensions of panels A' and E' be less than ½ the lateral dimensions of panels B', C', and D' so that the drape will lie flat when folded, but long enough so that when the longitudinal edges are grasped to unfold contact will be made only with the sterile area of the drape.

Figure 6:
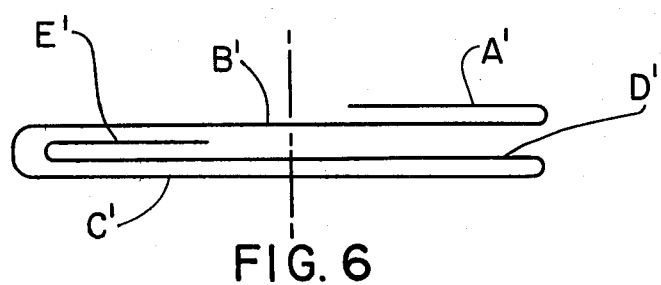
FIG. 6 is a cross sectional view and FIG. 7 a top plan view of the longitudinally folded drape.
Figure 7:
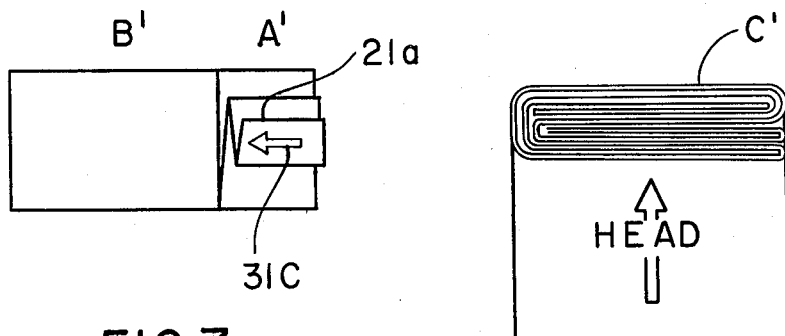

For the convenience in describing longitudinal folding the surface with panel K will be designated the top surface and the opposite surface the bottom surface. The drape is folded between panels A', B', C', D', and E' so that the top surface of panel D' rests on the top surface of panel C', the bottom surface of panel E' rests on part of the bottom surface of panel D'; the top surface of panel B' rests on the top surface of panel E' and the remaining exposed surface of panel D', and the bottom surface of panel A' rests on part of the bottom surface of panel B'. FIG. 6 shows a side view of the folded drape and FIG. 7 a top view. However, the order of folding is not important and panels B' and A' may be folded first rather than panels D' and E' to form the folded drape.

Figure 8:
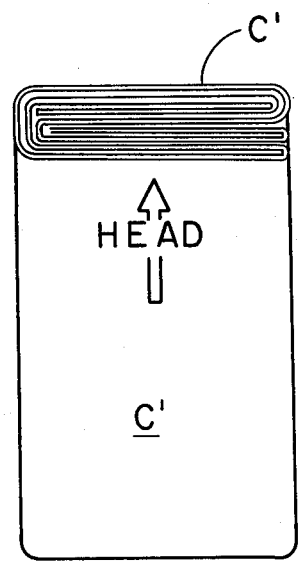
FIG. 8 is a perspective view of the completely folded drape indicating the directional arrow on the outside.

The drape as folded may be packaged and sterilized or may be additionally longitudinally folded in half with the bottom surface of panel C' exposed on the outside as illustrated by the dotted line in FIG. 6. The drape in its final form is shown in FIG. 8. It is properly labelled for identification and to indicate direction of placement during application of the drape the word "Head" with an arrow pointed in the direction of end edge 21b are also printed on the drape. However, any method to identify and indicate direction of placement may be used.

Application of the Drape to the Patient

Referring now to FIGS. 9-15, there is illustrated a method of applying the bilateral split drape, folded as previously described, to a patient about to undergo surgery requiring exposure of both legs. The method will accomplish rapid and efficient application while keeping operating surfaces and personnel out of contact with the highly contaminated perineal area.

Figure 9:
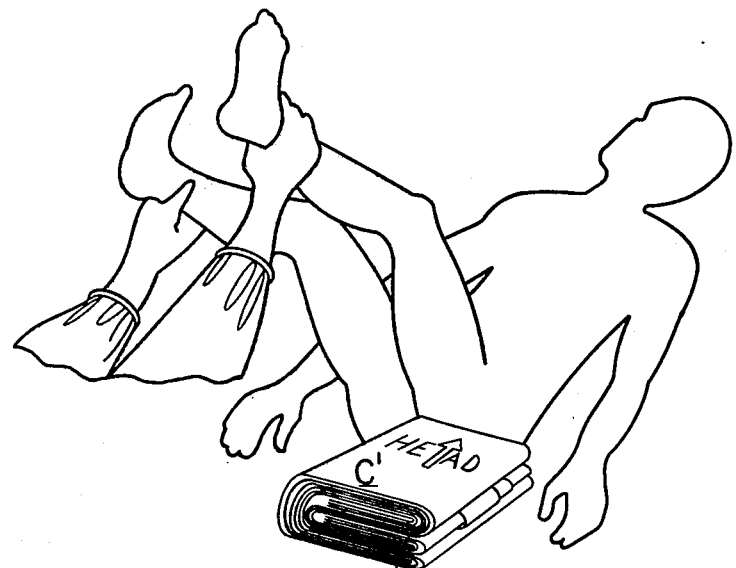
FIG. 9 is a perspective view of the folded drape being placed under a patient.
Figure 10:
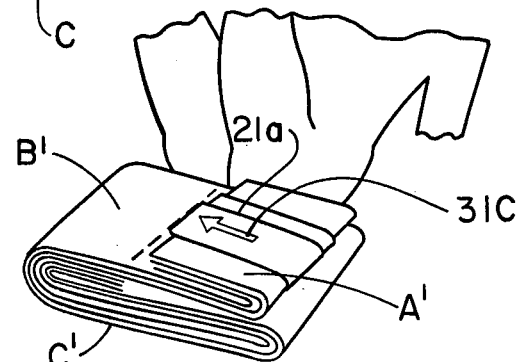
FIGS. 10-13 are perspective views showing the drape being unfolded.
Figure 11:
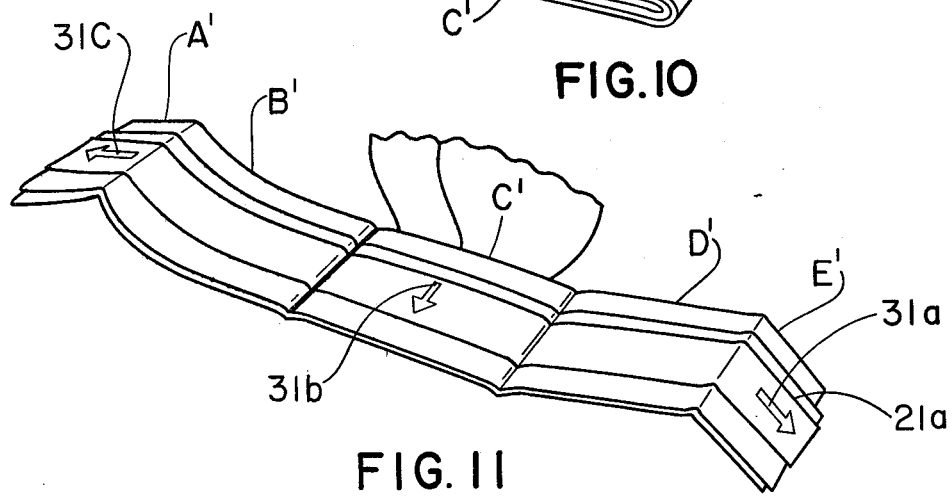
Figure 12:
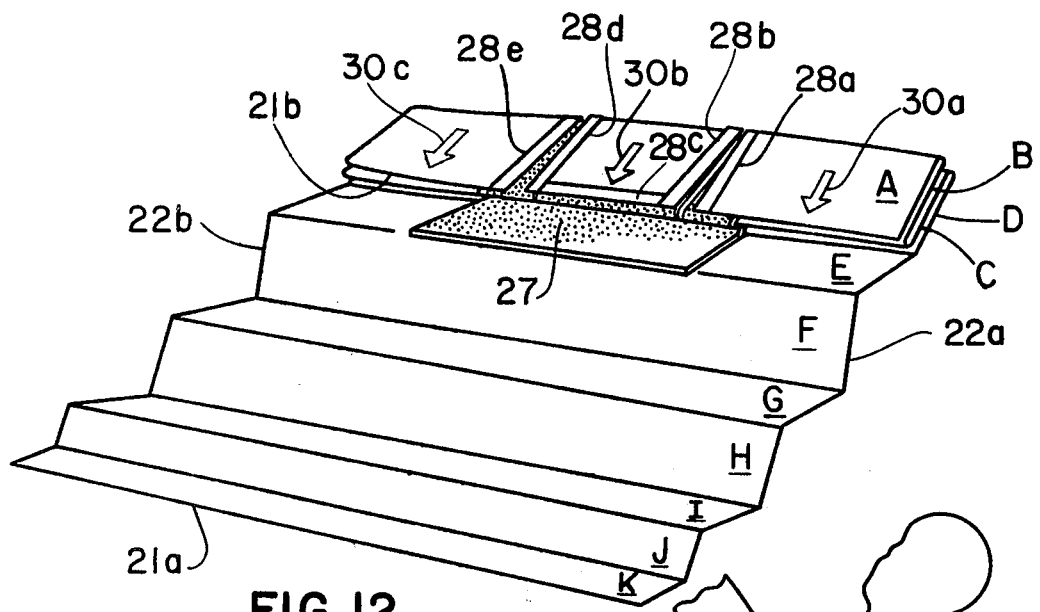
Figure 13:
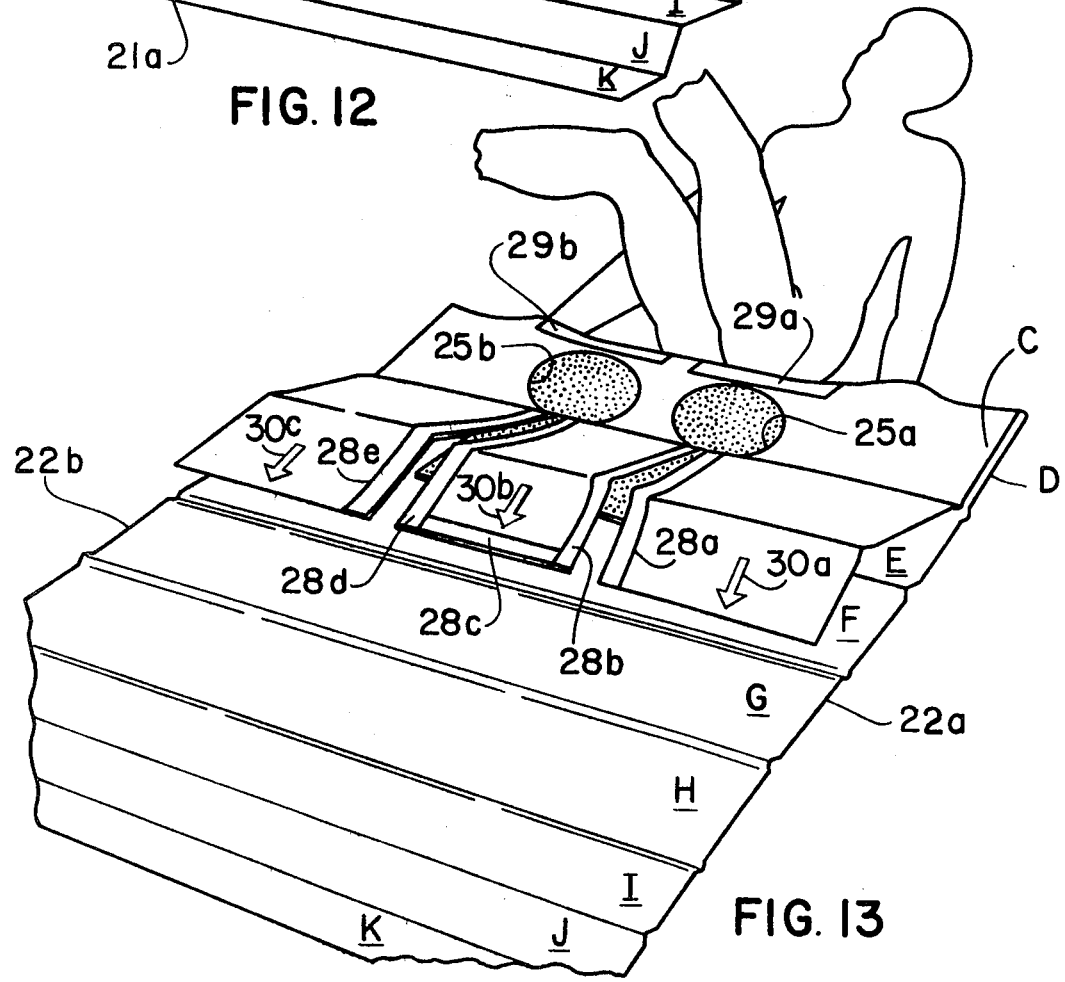
Figure 14:
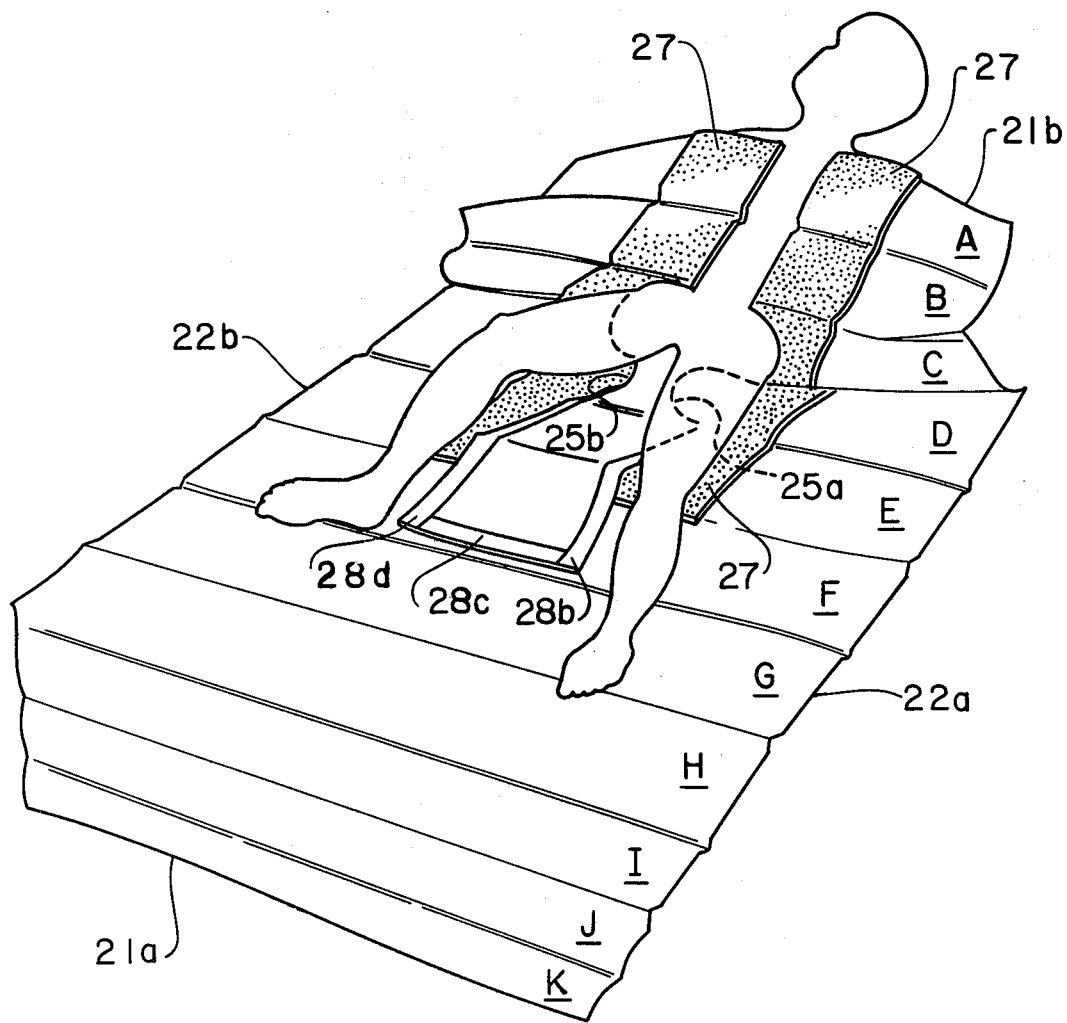
FIG. 14 and 15 are perspective views showing the final steps in drape application to the patient.
Figure 15:
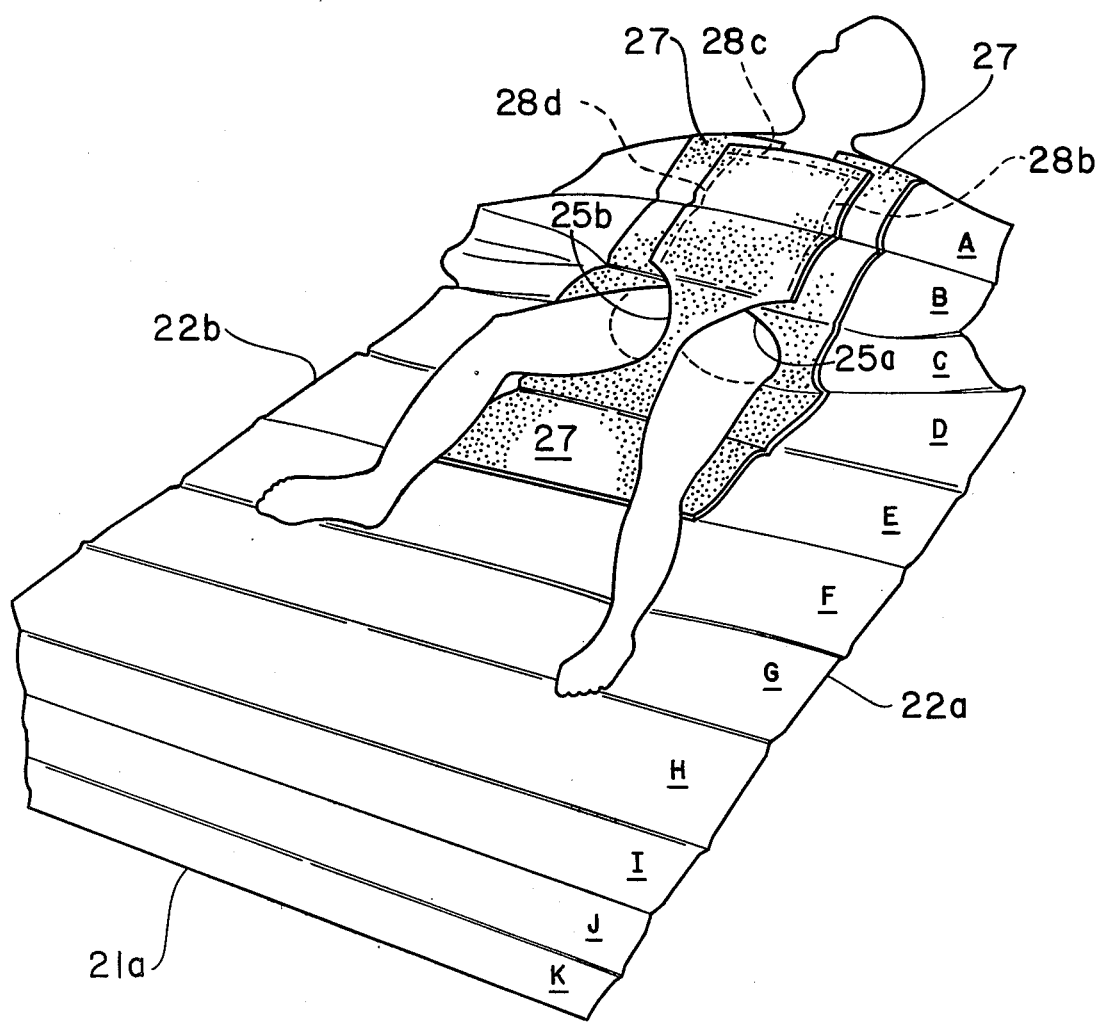

After the patient has been prepared for surgery on the operating table an assistant on each side of the table lifts one of the patient's legs upwardly. The folded drape is then placed on the operating table near the patient's body arranged so the arrow designated "Head" printed on the folded drape points towards the patient's head as shown in FIG. 9. While the patient's legs are still upwardly raised the first half fold of the drape is opened out as in FIG. 10 and placed so that the center of the folded drape is aligned with the midline of the patient's body. Then the drape is grasped where indicated by arrows 31a and 31c and panels A' and B', then E' and D' are opened out as shown in FIG. 11 so that all longitudinal folds are flat. Still maintaining the legs upwardly raised, the drape is grasped at the center arrow 31b and end edge 21a is pulled away from the patient in the direction of the arrow to unfold lateral panels E through K as shown in FIG. 12. Next at arrows 30a, 30b and 30c, end edge 21b is pulled away from the patient in the direction of the arrows to unfold panels A, B, and C so that the only fold remaining in the drape is the lateral fold between panels C and D, as shown in FIG. 13. At this point all peel release liners are removed to expose the tacky surface of the adhesive strips. Adhesive strips 29a and 29b are secured to the underside of the patient's upraised legs at a point proximal enough to expose the portion of the legs needed for the particular surgical procedure. Next the two outer flaps formed by the fenestrations in lateral panels A, B, and C are lifted up and around the outside of each leg and secured to the torso of the patient slightly toward the midline, as shown in FIG. 14. The central flap of panels A, B, and C is then brought up between the legs, at which point the legs can be lowered onto the operating table. The central flap is then secured to the torso of the patient and overlaps portions of the two end flaps, as shown in FIG. 15. The order of placing the flaps, however, is not critical and the central flap may be secured to the patient first, then the side flaps placed to overlap the central flap. During some surgical procedures it may also be desired to place stockings on the distal portions of the legs.

The foregoing detailed description is given for clearness of understanding only, and no unnecessary limitations should be understood therefrom, as modifications will be obvious to those skilled in the art.

I claim:

1. A disposable surgical drape for bilateral leg surgery comprising:
   (a) a nonwoven sheet having side edges and end edges, the sheet having two substantially parallel fenestrations defining operative sites through each of which a leg of a patient may be exposed, said fenestrations having an open end and a closed end, said open end opening onto one end edge and said fenestrations extending longitudinally toward the middle of the sheet substantially parallel to the side edges with said closed ends being shaped to accomodate the patient's legs, the fenestrations being spaced apart forming a central flap that conforms to the spacing between a patient's legs;
   (b) an absorbent, fluid impervious laminate attached to one surface of the nonwoven sheet, the laminate substantially surrounding the fenestrations in the nonwoven sheet, the laminate having two fenestrations conforming to and aligned with the two fenestrations in the sheet;
   (c) tacky pressure sensitive adhesive on the surface of the nonwoven sheet opposite the laminate adjacent the edges and closed end of each said fenestrations; and
   (d) removable adherent release strips covering the pressure sensitive adhesive whereby, once said drape is in use, both the patient's legs may be exposed through said fenestrations while the perineal area is covered by said central flap.

2. The drape of claim 1 wherein each fenestration opening has a circular shape at the innermost end from said end edge of the sheet with a slit extending from the circular element of each fenestration connecting it to said end edge of the sheet, the circular shape opening defining the circumference of the leg to provide a closer fit of the drape with less bulk and overlap.

* * * * *